(12) United States Patent
Takei et al.

(10) Patent No.: US 9,718,024 B2
(45) Date of Patent: Aug. 1, 2017

(54) METHOD FOR PREVENTING INACTIVATION OF FLUE GAS DESULFURIZATION APPARATUS

(75) Inventors: Noboru Takei, Kanagawa (JP); Chisa Nishizaki, Kanagawa (JP)

(73) Assignee: Chiyoda Corporation, Yokohama-shi (JP)

( * ) Notice: Subject to any disclaimer, the term of this patent is extended or adjusted under 35 U.S.C. 154(b) by 660 days.

(21) Appl. No.: 14/241,112

(22) PCT Filed: Aug. 22, 2012

(86) PCT No.: PCT/JP2012/071160
§ 371 (c)(1),
(2), (4) Date: Feb. 17, 2015

(87) PCT Pub. No.: WO2013/031595
PCT Pub. Date: Mar. 7, 2013

(65) Prior Publication Data
US 2015/0174525 A1 Jun. 25, 2015

(30) Foreign Application Priority Data
Aug. 30, 2011 (JP) .................. 2011-187054

(51) Int. Cl.
*B01D 53/34* (2006.01)
*B01D 53/50* (2006.01)
(Continued)

(52) U.S. Cl.
CPC .......... *B01D 53/346* (2013.01); *B01D 53/48* (2013.01); *B01D 53/501* (2013.01); *F23J 15/02* (2013.01);
(Continued)

(58) Field of Classification Search
CPC .... B01D 53/346; B01D 53/48; B01D 53/501; B01D 53/34; B01D 2251/13;
(Continued)

(56) References Cited

U.S. PATENT DOCUMENTS 4,431,618 A * 2/1984 Boward, Jr. ......... B01D 53/501
422/62
7,288,233 B2 * 10/2007 Breen .................... B01D 53/64
423/210

FOREIGN PATENT DOCUMENTS

| JP | 06-086910 A | | 3/1994 | |
| JP | 2002-174406 | * | 6/2002 | |
| WO | WO 2011065118 A1 | * | 6/2011 | ............. B01D 53/30 |

OTHER PUBLICATIONS

JP2002-174406, 2002, Goto et al, see machine translation in english.*

(Continued)

*Primary Examiner* — Melvin C Mayes
*Assistant Examiner* — Smita Patel
(74) *Attorney, Agent, or Firm* — Locke Lord LLP

(57) ABSTRACT

To provide a method for predicting a deactivation phenomenon in a flue-gas desulfurization unit to prevent the occurrence of the deactivation phenomenon before it happens.
There is provided a method for preventing the occurrence of a deactivation phenomenon in a flue-gas desulfurization unit that treats flue gas of a coal-fired boiler, the method includes calculating a deactivation potential as an index of the deactivation phenomenon based on alkaline components such as Na, Ca, Mg, and K contained in ash in the flue gas, and performing an operation management, such as adjustment of set value of a pH control system, on the flue-gas desulfurization unit depending on change of the deactivation potential.

8 Claims, 8 Drawing Sheets

(51) Int. Cl.
*F23J 15/02* (2006.01)
*B01D 53/48* (2006.01)
*G01N 33/00* (2006.01)

(52) U.S. Cl.
CPC ... *G01N 33/0004* (2013.01); *B01D 2251/304* (2013.01); *B01D 2251/404* (2013.01); *B01D 2258/0283* (2013.01); *F23J 2215/20* (2013.01)

(58) Field of Classification Search
CPC ........ B01D 2251/302; B01D 2251/306; B01D 2251/14; B01D 2251/402; B01D 2251/404; B01D 2251/304; G01N 33/0004; G01N 33/00; F23J 2700/00; F23J 2700/01; F23J 2700/02; F23J 2700/03; F23J 2215/20; F23J 15/02
See application file for complete search history.

(56) References Cited

OTHER PUBLICATIONS

International Search Report dated Nov. 6, 2012, issued for PCT/JP2012/071160.

\* cited by examiner (a)

(b)

(a)

(b)

(c)

(a)

(b)

METHOD FOR PREVENTING INACTIVATION OF FLUE GAS DESULFURIZATION APPARATUS

TECHNICAL FIELD

The present invention relates to a method for preventing the occurrence of a deactivation phenomenon in a flue-gas desulfurization unit.

BACKGROUND ART

A coal-fired power plant has a flue-gas desulfurization unit for treating flue gas so as to remove sulfur oxides ($SO_x$) generated by combustion of coal in a boiler. Various types of wet- or dry-type flue gas desulfurization units have been proposed, but a wet coal gypsum limestone-gypsum method is conventionally often used because cheap limestone can be used as a desulfurizing agent and a relatively high sulfur removal ratio can be achieved (Patent Literature 1).

The limestone-gypsum method is performed by bringing flue gas into gas-liquid contact with an absorbent in slurry state containing finely-powdered limestone to allow the absorbent to absorb $SO_2$ gas contained in the flue gas. Then, $SO_2$ is fixed as gypsum in the absorbent by a reaction represented by the following formula 1 to remove sulfur oxides.

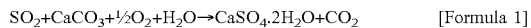
$$SO_2 + CaCO_3 + \tfrac{1}{2}O_2 + H_2O \rightarrow CaSO_4 \cdot 2H_2O + CO_2 \quad \text{[Formula 1]}$$

In the limestone-gypsum method, the gas-liquid contact between the absorbent and the flue gas can be efficiently performed using, for example, a reactor equipped with a sparger pipe (a jet-bubbling reactor). More specifically, the reactor is filled with the absorbent so that the tip of the sparger pipe is submerged therein, and then the flue gas is discharged from the tip of the sparger pipe into the absorbent. By doing so, the flue gas rises as fine bubbles in the absorbent, during which gas-liquid contact between the absorbent and the flue gas is efficiently performed at the interface of each bubble.

Sulfur oxides absorbed by the gas-liquid contact are oxidized to sulfuric acid and at the same time, it is neutralized by the absorbent in which limestone is dissolved so that gypsum is produced. The slurry containing the thus produced gypsum is extracted from the reactor, sent to a solid-liquid separation means such as a centrifugal separator, and separated into granular gypsum and a liquid fraction. Part of the separated liquid fraction is returned to the flue-gas desulfurization unit, and the rest is sent to a wastewater treatment unit and further treated.

CITATION LIST

Patent Literature

Patent Literature 1: Japanese Patent Application Laid-Open (JP-A) No. 6-086910

SUMMARY OF INVENTION

Technical Problem

Flue gas of a coal-fired boiler contains not only the above-described sulfur oxides but also nitrogen oxides, ash and so on. They are removed by a denitration unit and an electric dust collector provided upstream of a flue-gas desulfurization unit, but a small part of the ash passes through these denitration unit and electric dust collector, reaches the flue-gas desulfurization unit and is mixed into an absorbent of the flue-gas desulferization unit. The ash mixed into the absorbent is gradually dissolved, and then sometimes forms an inert film (apatite) on the surface of limestone so that the limestone as a desulfurizing agent is deactivated.

The occurrence of the above-described deactivation of limestone degrades desulfurization performance, and therefore as measures against it, adjustment of pH of the absorbent and addition of a chemical agent such as $Na^+$ are performed. However, these measures are taken after such a deactivation phenomenon is confirmed, and therefore there was a case where desulfurization performance was significantly degraded due to delay in taking action or a case where frequent operational adjustments were necessary due to a failure to take appropriate action. These cases impaired the reliability of the desulfurization unit.

In general, ash mainly contains alumina ($Al_2O_3$) or silica ($SiO_2$), and contains CaO, MgO, $Na_2O$, $K_2O$, and the like other than them. The elution rate of a solid is generally proportional to the specific surface area of the solid, and the content and the diffusion coefficient of a soluble material contained in the solid. It is therefore supposed that an elution rate of Al, which causes a deactivation phenomenon, can be also estimated from these factors to some extent.

However, when ashes remaining after combustion of bituminous coal and PRB coal were sampled and mixed with and dissolved in an absorbent, there was a case where these two kinds of ashes have large differences in their dissolution rate even though they are considered to have substantially the same dissolution rate (in an experimental stage, sometimes referred to as "elution rate") judging from their total Al content and specific surface area. Alternatively, there was a case where one of the ashes considered to have a lower dissolution rate than the other contrarily had a higher dissolution rate. Therefore, the present inventors have considered that there is a factor, other than the above-described specific surface area, soluble material content and the like, which has an influence on the solubility and have extensively studied.

As a result, it has been found that the solubility is influenced not only by the total Al content in ash but also by a vitrification ratio, which represents how much of minerals contained in ash are present as glass (amorphous), and the atomic arrangement structure of glass. Further, it has also been found that ash information such as Al content can effectively predict a deactivation phenomenon caused by Al eluted under the influence of the vitrification ratio and the atomic arrangement structure of glass, which makes it possible to prevent the occurrence of the deactivation phenomenon. This has led to the completion of the present invention.

Solution to Problem

Namely, the present invention provides a method for preventing occurrence of a deactivation phenomenon in a flue-gas desulfurization unit that treats flue gas of a coal-fired boiler. The method includes calculating a deactivation potential as an index of the deactivation phenomenon based on an alkaline component contained in ash in the flue gas, and performing an operation management of the flue-gas desulfurization unit depending on change of the deactivation potential.

Advantageous Effects of Invention

According to the present invention, it is possible to predict a deactivation phenomenon in a flue-gas desulfurization unit and to prevent its occurrence before it happens, which makes it possible to improve the reliability of the flue-gas desulfurization unit.

DESCRIPTION OF EMBODIMENTS

Figure 1:
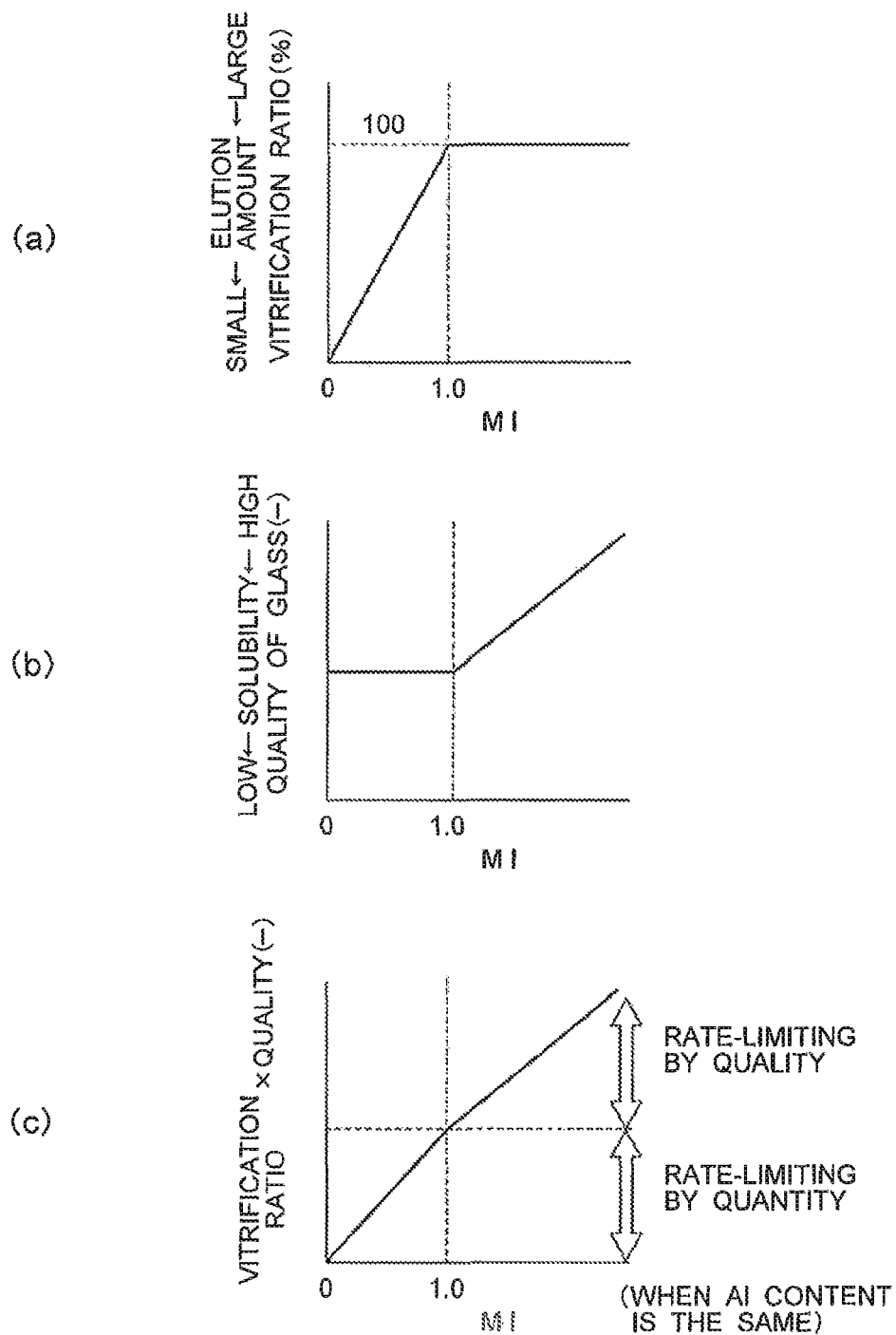
FIG. 1 shows graphs representing the relationships between MI, which is a basic index in a method for preventing a deactivation phenomenon according to the present invention, and a vitrification ratio or the quality of glass.

Coal used as fuel for a coal-fired boiler contains, in its inside or on its surface, inorganic substances such as Si-based quartz ($SiO_2$), Si—Al-based kaolinite ($Al_2Si_2O_5(OH)_4$), smectite containing Na, Ca, and Mg, illite containing K, and calcite ($CaCO_3$). These inorganic substances are exposed to a high temperature atmosphere during combustion of hydrocarbons as a main component of coal so that some of them are melted and then turned into fly ash containing glass by cooling.

For example, part of quartz contained in coal remains in its original crystalline state without change, and the rest is melted alone or with other minerals and then solidified and turned into glass. Kaolinite, smectite, Me, and calcite are almost completely melted so that crystals such as mullite ($3Al_2O_3 \cdot 2SiO_2$) and the like are formed or glasses such as $CaAl_2Si_2O_8$ or $Ca_2Al_2Si_2O_9$ and the like are formed.

It is considered that such crystallization behavior and vitrification behavior are due to the effect of alkaline components, such as Na, Ca, Mg, and K, contained in minerals (hereinafter, these components will be also referred to as "modifier"). More specifically; it is considered that when the amount of the modifier is larger, vitrification is more promoted so that ash with higher vitrification ratio is obtained. When ash has a higher vitrification ratio, its solubility becomes higher.

The reason why the amount of the modifier is considered to have an influence on the above-described vitrification ratio is that it is considered that when the amount of the modifier is increased, the chances that the modifier enters a crystalline network structure are increased so that its network is distorted or cleaved and therefore the network structure is collapsed. That is, it is considered that the presence of the modifier makes the network structure of atomic arrangement more random so that melt viscosity is reduced and therefore vitrification is likely to occur during cooling.

Further, it is considered that the quality of glass varies due to the difference in type or content of a modifier contained in ash. This results from a condition that a mixture of a solid phase and a liquid phase mainly has a three-dimensional structure when the modifier is absent, but as the amount of the modifier is increased, the ratio of a layer structure or a chain structure is relatively increased.

It is considered that as the ratio of a layer structure or a chain structure is increased, the amount of nonbridging oxygen present at cleavage sites in the network structure is increased so that the solubility of ash is increased. It is to be noted that the amount of nonbridging oxygen is higher in a chain structure than in a layer structure, and therefore the chain structure has higher solubility than the layer structure.

As described above, differences in the degree of vitrification ratio and the atomic arrangement structure of glass causes a difference in the solubility of ash (fly ash), which causes a difference in the likelihood of a deactivation phenomenon. Therefore, it is considered that prior knowing of the vitrification ratio of ash and the atomic arrangement structure of glass in ash, as ash information, can predict the occurrence of a deactivation phenomenon.

The present inventors have contemplated to introduce a deactivation potential as an index for determining the possibility of occurrence of a deactivation phenomenon, and also contemplated to use the deactivation potential for representing the vitrification ratio of ash and the atomic arrangement structure of glass and finally representing the solubility of ash. The present inventors have focused attention on Al, Si, and the modifier contained in fly ash as factors that have an influence on the deactivation potential, and have tried to represent the deactivation potential by using a modifier index (hereinafter, also referred to as "MI") that takes into account the ratio of the modifier (i.e., alkaline components) to Al or Si. As a result, it has become possible to very easily and effectively predict a deactivation phenomenon and thus prevent its occurrence.

More specifically, as represented by the following formula 2, the concept of deactivation potential has been first introduced as a factor that has an influence on the dissolution rate of Al contained in ash.

Dissolution rate of Al∝diffusion coefficient×specific surface area×deactivation potential  [Formula 2]

Then, as represented by the following formula 3, it has been considered that the deactivation potential is represented by the product of the Al content of ash, a quantitative factor, and a qualitative factor.

Deactivation potential=Al content of ash×quantitative factor×qualitative factor  [Formula 3]

Further, it has been considered that each of the quantitative factor and the qualitative factor in the above formula 3 correlates with an MI defined by the following formula 4.

MI=(2Ca+2αMg+βNa+γK)/Al,  [Formula 4]

wherein Ca, Mg, Na, K, and Al each represent its molarity in fly ash. The reason why Ca and Mg have a coefficient of 2 is that Ca and Mg among the above 4 kinds of alkaline components are considered to constitute glass whose composition is close to $MAl_2Si_2O_8$, and Na and K are considered to constitute glass whose composition is close to $MAlSi_3O_8$ (here, M represents Ca, Mg, Na, or K).

α, β, and γ are MI weighting coefficients for the alkaline components based on Ca, and were determined from modification degree ratios and ionic radius ratios in consideration of the possibility of occurrence of distortion or cleavage in the network structure of glass. The modification degree ratio indicates how much of the alkaline component is present in high degree of freedom without bonding to an oxygen ion, and can be determined from, for example, a bond energy with oxygen. Here, based on the bond energy with oxygen, the modification degree ratios of Ca and Mg were set to 1 and the modification degree ratios of Na and K were set to 2.

Further, it can be considered that a larger ionic radius is more likely to cause distortion of the network structure of glass, and therefore the ionic radius ratio among Ca, Mg, Na, and K, that is, Ca:Mg:Na:K=1:0.75:2.04:1.33 was adopted. From the product of the modification degree ratio and the ionic radius ratio, α=0.75, β=2.04, and γ=2.67 are obtained. That is, MI is represented by the following formula 5.

$$MI=(2Ca+1.5Mg+2.04Na+2.67K)/Al \quad \text{[Formula 5]}$$

By defining MI as described above, both the quantitative factor and the qualitative factor in the above formula 3 which have an influence on the solubility of ash can be represented using MI. First, the relationship between the degree of the vitrification ratio, which is the quantitative factor of glass, and MI will be described. For example, assuming that ash contains only Ca as a modifier, Mg, Na, and K in the above formula 5 are 0, and therefore MI=2Ca/Al.

If the analysis of the e ash shows that Ca/Al is 0.5, Ca and Al stoichiometrically saturate bulk glass whose composition is $CaAl_2Si_2O_8$. Therefore, it can be considered that all the amount of Al contained in the ash is vitrified (that is, vitrification ratio=100%). That is, when MI=1, the vitrification ratio can be considered as 100%.

On the other hand, when the Ca content is 0, MI=0. In this case, the modifier is not present in ash at all, and therefore it can be considered that 100% of Al is crystallized as, for example, mullite. That is, when MI=0, the vitrification ratio can be considered as 0%. As for the relationship between MI and the vitrification ratio, the vitrification ratio is proportional to MI when MI is in the range of 0 to 1, and the vitrification ratio remains 100% when MI exceeds 1.

Mg, Na, and K other than Ca can be considered in the same manner as the above-described Ca, and therefore it can be considered that MI defined by the above formula 5 represents the vitrification ratio of ash containing Ca, Mg, Na, and K. A graph representing the above-described relationship between the vitrification ratio, which is the quantitative factor, and MI is shown in FIG. 1(a).

Hereinbelow, the relationship between the atomic arrangement structure of glass, which is the quantitative factor of glass, and MI will be described. It can be considered that as the ratio of the modifier to Al is increased, as described above, a layer structure or a chain structure other than a three-dimensional structure is increased as the atomic arrangement structure of glass. It can be therefore considered that the deactivation potential depends more significantly on the qualitative factor of glass as MI becomes higher.

Therefore, when MI is 1 or higher, the value of MI is directly adopted as the qualitative factor in the formula 3. It is to be noted that MI=1 is a theoretical limit of presence of a three dimensional structure, and when MI is less than 1, the above-described vitrification ratio that is the quantitative factor becomes rate-limiting. That is, when MI is less than 1, 1 is uniformly adopted as the qualitative factor in the formula 3 regardless of the value of MI. A graph representing the above-described relationship between the quality of glass, which is the qualitative factor, and MI is shown in FIG. 1(b). A graph obtained by combining FIG. 1(a) and FIG. 1(b) is shown in FIG. 1(c).

In order to determine that the above-described MI is significant as a parameter for the vitrification ratio of ash, data of various ashes analyzed by X-ray diffraction (XRD), scanning electron microscopy (SEM) or the like were collected and the relationships between MI and the vitrification ratio of Al-based minerals were plotted on the graph shown in FIG. 1(a). The results are shown in FIG. 2(a).

Figure 2:
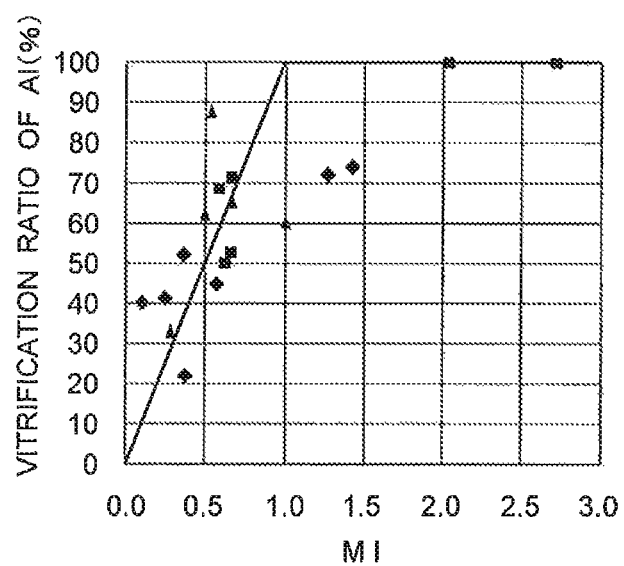
FIG. 2 shows graphs representing the relationships between MI, which is a basic index in a method for preventing a deactivation phenomenon according to the present invention, and the vitrification ratio of Al or Si.
Figure 2:
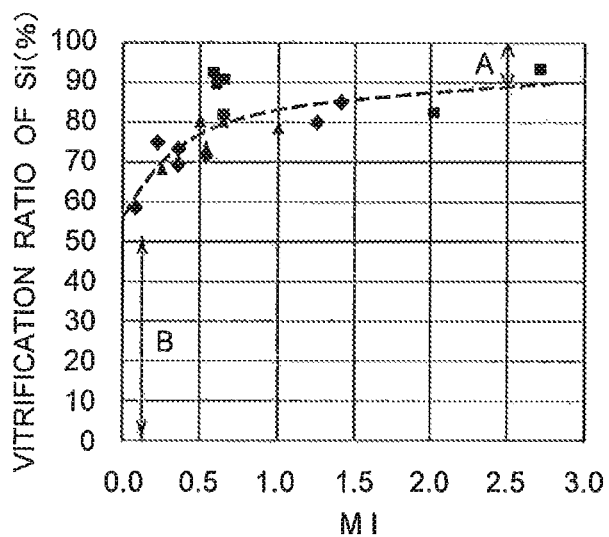

As can be seen from a graph shown in FIG. 2(a), when MI is in the range of 0 to 1, there are variations to some extent, but a correlation is observed almost along a straight line that passes through the origin and represents the proportional relation between MI and the vitrification ratio. In a region where MI exceeds 1, there are some variations but the vitrification ratio remains almost 100%. From the results, it has been found that the above-described method of representing the vitrification ratio of ash using MI as a parameter is significant.

Meanwhile, the above-described correlation shown in FIG. 1(a) represents the relationship between the vitrification ratio of Al contained in ash and MI, but if the vitrification ratio of Si contained in the ash can be estimated using this MI, deactivation can be more accurately predicted. Therefore, similarly to the above case, the relationships between MI and the vitrification ratio of Si-based minerals were plotted on the graph shown in FIG. 1(a) based on the data of various ashes analyzed by X-ray diffraction (XRD), scanning electron microscopy (SEM) or the like. The results are shown in FIG. 2(b).

As can be seen from FIG. 2(b), as indicated by A and B in the drawing, deflections from the graph shown FIG. 1(a) were caused, but a significant correlation was observed except for them. Therefore, as represented by, for example, the following formula 6, the vitrification ratio of a Si-based mineral contained in ash can also be estimated by multiplying MI determined based on Al by a coefficient F (MI) reflecting the difference between FIG. 2(a) and FIG. 2(b).

It is to be noted that the reason why the deflection indicated by A in FIG. 2(b) is caused is that 100% of Si cannot be vitrified because part of quartz ($SiO_2$) in coal remains as crystals without change. Further, the reason why the deflection indicated by B in FIG. 2(b) is caused is that, in a region where the value of MI is low, Si can be vitrified alone as $SiO_2$. Further, it is considered that SiAl glass is more likely to be affected by network scission caused by the modifier than simple Si glass and therefore the solubility is further improved.

$$\text{Dissolution rate of Si} \propto \text{diffusion coefficient} \times \text{specific surface area} \times \text{deactivation potential} \times F \text{ (MI)} \quad \text{[Formula 6]}$$

As described above, the use of the deactivation potential using MI as a parameter makes it possible to estimate the dissolution rate of Al or Si contained in fly ash. Further, the occurrence of a deactivation phenomenon can be predicted by performing the operation management of a flue-gas desulfurization unit based on the thus obtained dissolution rate of Al or Si, Which makes it possible to more rapidly and adequately respond to a deactivation phenomenon.

In order to respond to a deactivation phenomenon, which may occur in a flue-gas desulfurization unit, based on the dissolution rate of Al or Si obtained in such a manner as described above, for example, an alarm may be given when the dissolution rate of Al or Si determined by calculation by the above-described method exceeds its previously-set acceptable value. Alternatively, the set value of a control system for, for example, pH control of the flue-gas desulfurization unit may be automatically changed based on the dissolution rate determined by calculation by the above-described method.

Figure 3:
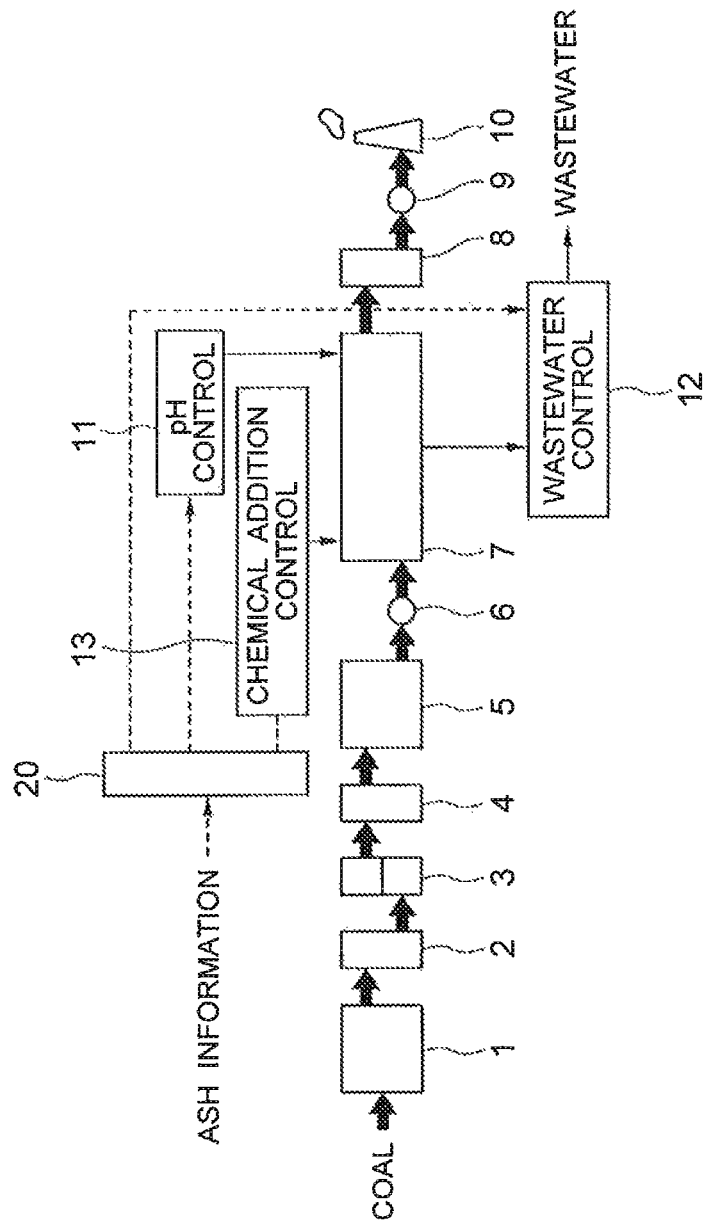
FIG. 3 is a block diagram showing one specific example of a controller according to the present invention incorporated into a flue-gas desulfurization unit.

For example, FIG. 3 shows an example of a series of flue-gas treatment facilities provided in a coal-fired power plant, in which a control system of a flue-gas desulfurization unit has the function of preventing the occurrence of a deactivation phenomenon. More specifically, the flue-gas treatment facilities shown in FIG. 3 are configured to treat flue gas discharged from a boiler 1 by a denitration unit 2, a dry electric dust collector 5, and a desulfurization unit 7 and then discharge it through a chimney 10.

Gas gas heaters 4 and 8 for heat recovery are provided upstream of the dry electric dust collector 5 and downstream of the desulfurization unit 7. Further, an air heater 3 is provided downstream of the denitration unit 2, and a blower 6 is provided upstream of the desulfurization unit 7 and a blower 9 is provided upstream of the chimney 10. In the flue-gas treatment facilities shown in FIG. 3, a controller 20 such as a CPU performs operations for predicting the occurrence of a deactivation phenomenon, and based on the results of the operations, signals are sent to a pH control system 11, a wastewater control system 12, and a chemical addition control system 13 of the desulfurization unit 7.

Figure 4:
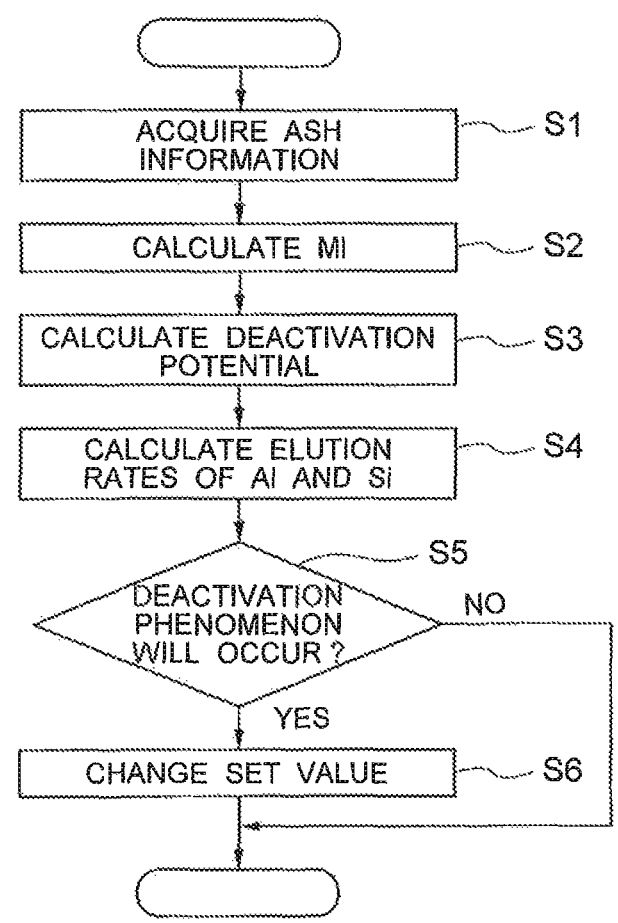
FIG. 4 is a flow chart showing one example of an algorithm executed in the controller according to the present invention.

The controller 20 executes, for example, an algorithm represented by a flow chart shown in FIG. 4. More specifically, first, ash information such as Al content and modifier content is acquired (acquisition means S1), and based on this information, an MI is calculated (MI calculation means S2). Then, a deactivation potential is determined from the MI (deactivation potential calculation means S3), and elution rates of Al and Si are calculated (elution rate calculation means S4). The presence or absence of the occurrence of a deactivation phenomenon is determined by making a comparison between the elution rates and their respective previously-set threshold values (comparison means S5).

When it is judged that at least one of the elution rates is higher than its threshold value, the pH control system 11, the wastewater control system 12, and/or the chemical addition control system 13 are/is changed in set value (set-value changing means S6). More specifically, when it is judged that the elution rate is higher than its threshold value, the pH control system 11 decreases a pH value to relatively increase the dissolution rate of limestone. The wastewater control system 12 increases the amount of wastewater to decrease the concentration of Al. The chemical addition control system 13 adds a chemical (for example, $Na^+$) to relatively decrease the concentration of Ca. On the other hand, when the calculated elution rates are equal to or lower than their threshold values, these controls are performed without changing the set values. This makes it possible to more rapidly and effectively respond to deactivation.

Figure 5:
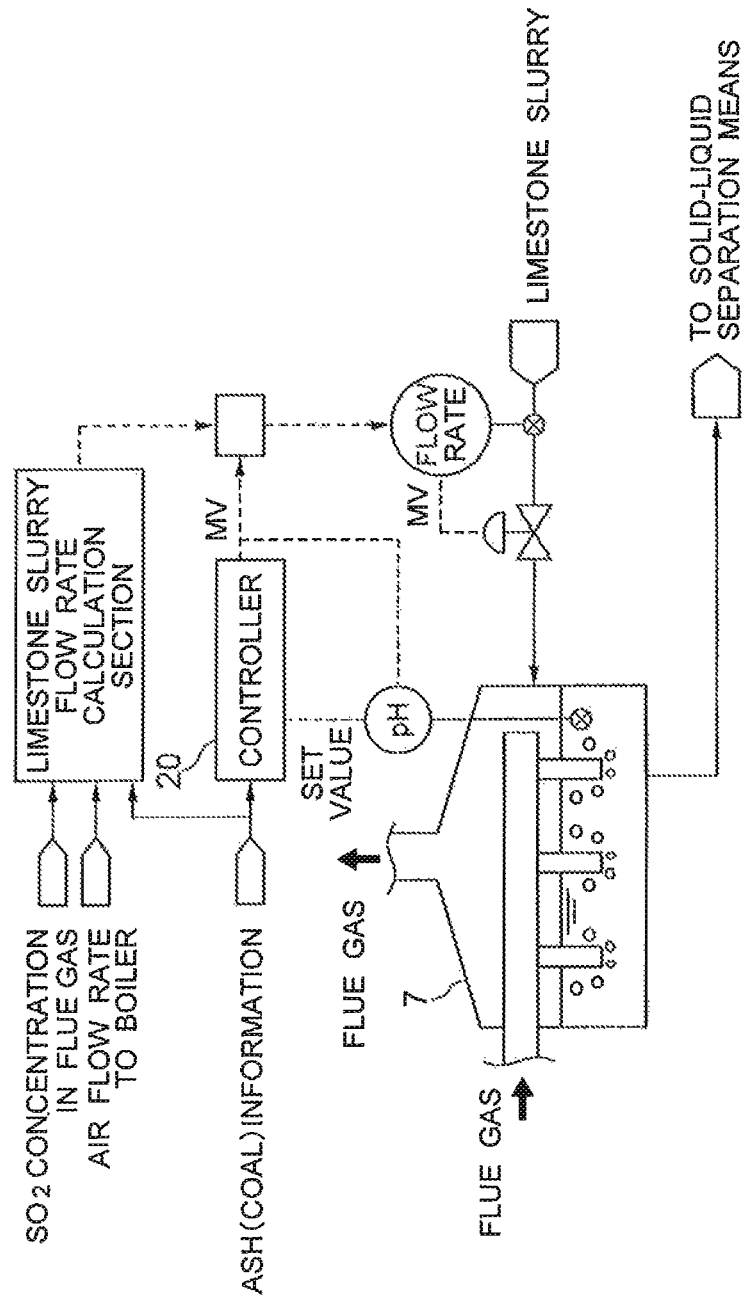
FIG. 5 is a schematic flow chart showing one specific example where the controller according to the present invention is incorporated into a pH control system of the flue-gas desulfurization unit.

FIG. 5 illustrates a case where the controller 20 executing the above-described algorithm is applied to the pH control system 11 of the desulfurization unit 7. In this case, when the comparison means S5 judges that either of the elution rates is higher than its threshold value, the set value of pH is changed to a predetermined value, and this new set value of pH is set as a target value to control the flow rate of limestone slurry to be supplied.

Although the method for preventing a deactivation phenomenon and the controller of a flue-gas desulfurization unit having the function of preventing the deactivation phenomenon according to the present invention have been described above with reference to their specific examples, the present invention is not limited to these specific examples, and various changes and modifications can be made without departing from the scope of the present invention. For example, in the above description, information as a base for MI is obtained from fly ash, but it may be obtained from fuel coal.

EXAMPLES

Example 1

Bulga coal, Yukaryo/NL coal, PRB coal, and bituminous coal were combusted in a coal-fired boiler separately from one another, and then their respective fly ashes were collected from a downstream electric dust collector. These four kinds of fly ashes were analyzed to measure their respective alumina contents, silica contents, and modifier contents. Then, the molarities of Ca, Mg, Na, K, and Al were determined from the measurement results and substituted into the above formula 5 to calculate the MI of each of the fly ashes. From the thus obtained MI, the vitrification ratio of Al (quantitative factor) and the qualitative factor of glass were determined according to FIG. 1(a) and FIG. 1(b).

Figure 6:
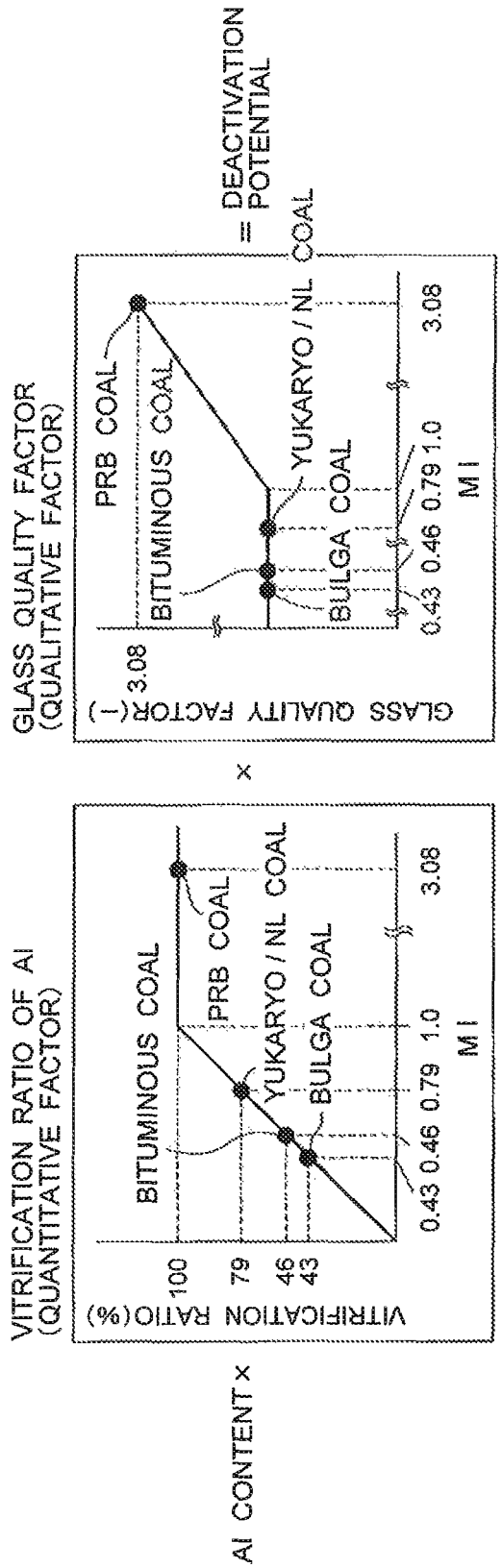
FIG. 6 shows a formula for calculating a deactivation potential in one specific example of the method for preventing a deactivation phenomenon according to the present invention, wherein a vitrification ratio and the quality of glass are represented by graphs using MI as a parameter.

Further, as for Si, the vitrification ratio of Si was determined from the above-described MI based on FIG. 2(b) to determine a Si glass content. The thus obtained Al content, MI, vitrification ratio of Al, Al glass content, quality of Al glass, and deactivation potential of the respective fly ashes are shown in the following Table 1. Further, a calculation formula is shown in FIG. 6 using graphs, which represents the process of determining the vitrification ratio (quantitative factor) and the qualitative factor of glass using MI as a parameter and then calculating the deactivation potential from them. It is to be noted that the vitrification ratio of Si sometimes increases the elution rate of Al.

TABLE 1

| | Type of coal | | | |
| --- | --- | --- | --- | --- |
| | Bulga coal | Yukaryo/Nl coal | PRB coal | Bituminous coal |
| Al content as $Al_2O_3$ (wt %) | 18 | 24 | 20 | 31 |
| MI | 0.43 | 0.79 | 3.08 | 0.46 |
| Vitrification ratio of Al (%) | 43 | 79 | 100 | 46 |
| Al glass content (wt %) | 8 | 19 | 20 | 14 |
| Qualitative factor of Al glass | 1 | 1 | 3.08 | 1 |
| Deactivation potential | 8 | 19 | 62 | 14 |

As shown in Table 1, when the Al glass content is used as an index it distributes only in a narrow range from a minimum value of 8 to a maximum value of 20, but when the deactivation potential is used as an index, it shows a wide distribution from a minimum value of 8 to a maximum value of 62. Therefore, it has been found that characterizing ash by deactivation potential using MI as a parameter is significant.

Example 2

Attempts were made to determine the possibility of predicting the occurrence of a deactivation phenomenon in an actually operating flue-gas desulfurization unit with the use of the Al content; the vitrification ratio of Al, and the deactivation potential respectively. More specifically, fly ash contained in flue gas to be treated by a flue-gas desulfurization unit was regularly sampled and analyzed to determine its alumina content and modifier content.

Then, the molarities of Ca, Mg, Na, K, and Al were determined from the analysis values and substituted into the above formula 5 to calculate MI. Further, from the obtained value of a vitrification ratio was determined using FIG. 1(a). Further, the quality of glass was determined using FIG. 1(b), and it was substituted into the formula 3 together with the above-described vitrification ratio determined using FIG. 1(a) to determine deactivation potential.

Figure 7:
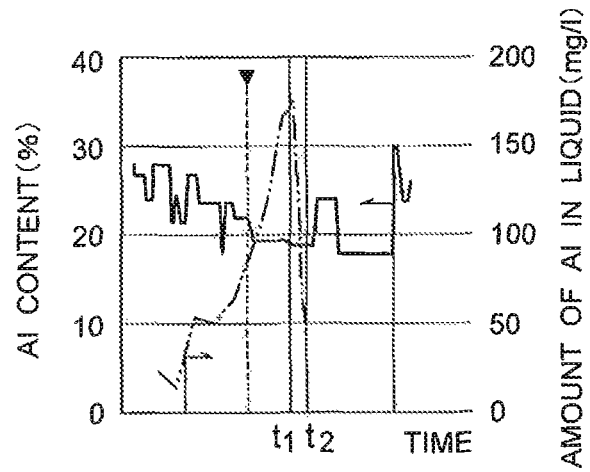
FIG. 7 shows graphs representing changes in the Al content of ash, the vitrification ratio of Al in ash, and deactivation potential together with a change in the Al concentration in an absorbent, wherein the abscissa represents time.
Figure 7:
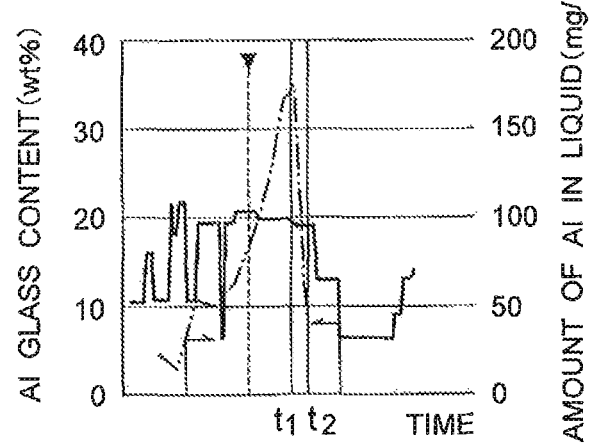
Figure 7:
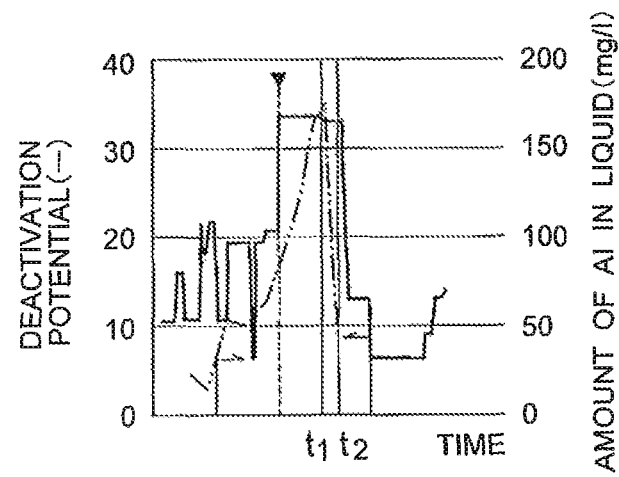

On the other hand, an absorbent was regularly sampled from the flue-gas desulfurization unit to measure the actual concentration of Al in the liquid. Then, attempts were made to predict the occurrence of a deactivation phenomenon in the flue-gas desulfurization unit after replacement of coal fuel with the use of the Al content of ash (FIG. 7(a)), the Al glass content of ash (FIG. 7(b)), and the deactivation potential (FIG. 7(c)) determined above, respectively As a result, when the Al content of ash was used as an index, as shown in FIG. 7(a), it showed a reverse trend from the actual concentration of Al in the liquid represented by a curve not only during normal operation but also after replacement of coal fuel indicated by an inverted delta symbol in the drawing. Therefore, it has been found that the Al content of ash cannot be used as an index for predicting a deactivation phenomenon.

Further, when the Al glass content of ash was used as an index, as shown in FIG. 7(b), it showed a trend generally similar to that of the actual concentration of Al in the liquid, but sensitivity was not high after replacement of coal fuel indicated by an inverted delta symbol in the drawing, and it has been found that it is difficult to use it as an index for predicting a deactivation phenomenon in view of measurement errors etc.

On the other hand, when the deactivation potential was used as an index, as shown in FIG. 7(c), it showed substantially the same pattern as the actual concentration of Al in the liquid both before and after replacement of coal fuel indicated by an inverted delta symbol in the drawing. Therefore, it has been found that the deactivation potential is very useful as an index for predicting a deactivation phenomenon. It is to be noted that a deactivation phenomenon occurred during time between $t_1$ and $t_2$ indicated on the abscissa.

Reference Example

PRB coal and Bulga coal (Bul coal) were combusted in a coal-fired boiler separately from each other, and their respective fly ashes were collected from a downstream electric dust collector. Each of the collected fly ashes was subjected to the following elution test More specifically, first, three slurries were prepared for each of the sampled fly ashes by weighing 1 g of the fly ash and adding it to 100 mL of water. These three slurries were made different in pH from one another using 1 mol/L sulfuric acid.

Figure 8:
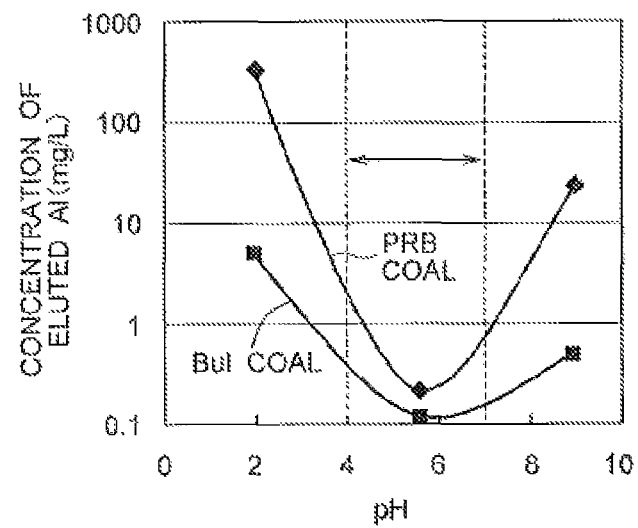
FIG. 8 shows graphs representing differences in Al elution rate or Si elution rate of two kinds of ashes.
Figure 8:
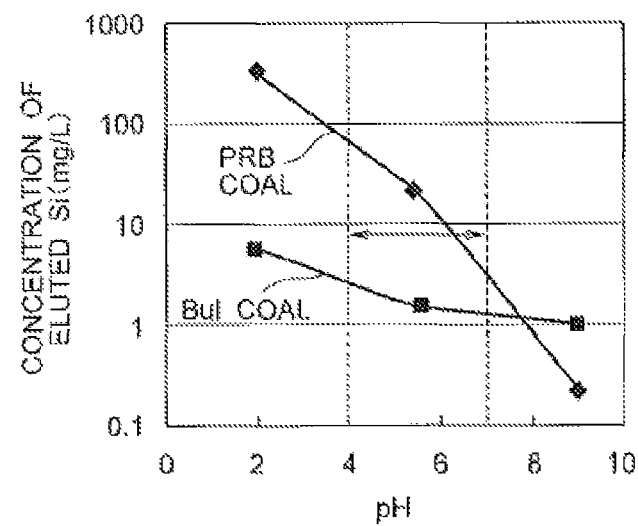

Each of the thus obtained slurries was stirred by a Teflon (Registered Trademark) blade stirrer to elute Al and Si. After the lapse of 30 minutes, 1 hour, and 6 hours from the start of stirring, a sample was taken and filtered, and filtrate was diluted to 200 mL to prepare an analysis object. The concentrations of Al and Si in the analysis object were analyzed using an ICP emission spectrometer. The results are shown in FIGS. 8(a) and 8(b). It is to be noted that the obtained results of analysis were almost the same irrespective of the elapsed time from the start of stirring, and therefore FIGS. 8(a) and 8(b) show the results of the samples analyzed after a lapse of 1 hour.

As can be seen from FIGS. 8(a) and 8(b), irrespective of the fact that the Al content of the fly ash of PRB coal was substantially the same as that of the fly ash of Bulga coal, the concentrations of both Al and Si eluted from the fly ash of PRB coal were higher than those of both Al and Si eluted from the fly ash of Bulga coal in a pH range of 4 to 7 (indicated by an arrow in the drawings) in which flue-gas desulfurization is generally performed. From the results, it has been found that there is it factor, other than the Al content, which has an influence on the elution rates.

REFERENCE NUMERALS

1 Boiler
2 Denitration unit
3 Air heater
4, 8 Gas gas heater
5 Dry electric dust collector
6, 9 Blower
7 Desulfurization unit
10 Chimney
20 Controller

The invention claimed is:

1. A method for preventing occurrence of a deactivation phenomenon in a flue-gas desulfurization unit that treats flue gas of a coal-fired boiler, the method comprising: calculating a deactivation potential as an index of the deactivation phenomenon based on alkaline components contained in ash in the flue gas; and performing an operation management of the flue-gas desulfurization unit depending on change of the deactivation potential.

2. The method for preventing a deactivation phenomenon according to claim 1, wherein the operation management is to make an adjustment of at least any of a pH control system, a wastewater control system, and a chemical addition control system of the flue-gas desulfurization unit.

3. The method for preventing a deactivation phenomenon according to claim 1, wherein the deactivation potential takes into consideration a vitrification ratio of the ash and an atomic arrangement structure of glass.

4. The method for preventing a deactivation phenomenon according to claim 1, wherein the deactivation potential is calculated using, as a parameter, a ratio of the alkaline components to a soluble material contained in the ash.

5. The method for preventing a deactivation phenomenon according to claim 2, wherein the deactivation potential takes into consideration a vitrification ratio of the ash and an atomic arrangement structure of glass.

6. The method for preventing a deactivation phenomenon according to claim 2, wherein the deactivation potential is calculated using, as a parameter, a ratio of the alkaline components to a soluble material contained in the ash.

7. The method for preventing a deactivation phenomenon according to claim 3, wherein the deactivation potential is calculated using, as a parameter, a ratio of the alkaline components to a soluble material contained in the ash.

8. The method for preventing a deactivation phenomenon according to claim 5, wherein the deactivation potential is calculated using, as a parameter, a ratio of the alkaline components to a soluble material contained in the ash.

* * * * *